United States Patent [19]

Godin et al.

[11] 4,140,966
[45] Feb. 20, 1979

[54] PARTICLE ANALYZING APPARATUS AND FLUID CIRCULATING SYSTEM THEREFOR

[75] Inventors: Thomas J. Godin, Ft. Lauderdale; Donald E. Feuquay, Jr., Miami, both of Fla.

[73] Assignee: Coulter Electronics, Inc., Hialeah, Fla.

[21] Appl. No.: 830,101

[22] Filed: Sep. 2, 1977

[51] Int. Cl.² ............................................. G01N 27/07
[52] U.S. Cl. ................................................. 324/71 CP
[58] Field of Search ............... 324/71 CP; 73/432 PS; 364/555

[56] References Cited

U.S. PATENT DOCUMENTS

| | | | |
|---|---|---|---|
| 3,688,191 | 8/1972 | Claps | 324/71 CP |
| 3,793,587 | 2/1974 | Thom et al. | 324/71 CP |
| 3,810,010 | 5/1974 | Thom | 324/71 CP |
| 3,831,087 | 8/1974 | Schulz et al. | 324/71 CP |
| 3,979,669 | 9/1976 | Godin | 324/71 CP |
| 4,070,617 | 1/1978 | Kachel et al. | 324/71 CP |

FOREIGN PATENT DOCUMENTS 2042474   3/1972   Fed. Rep. of Germany ...... 324/71 CP Primary Examiner—Gerard R. Strecker
Attorney, Agent, or Firm—Silverman, Cass & Singer, Ltd.

[57] ABSTRACT

A particle analyzing apparatus having an aperture retaining member positioned in a housing for obtaining signals from particles which pass through a scanning aperture. The aperture retaining member includes an elongate director tube into which the particles to be sensed are introduced for movement to and passage directly through the aperture. An aperture holder with the aperture provided therein is positioned at the terminus of the director tube but spaced a small distance therefrom to permit entry of ensheathing clean liquid within the space and passage of the ensheathing liquid through the aperture simultaneously with passage of the particles. The downstream side of the aperture is in liquid communication through a fluid circulating system with the upstream side thereof; a pump is interposed in the path of liquid communication between the upstream and downstream sides of the aperture to enable continuous recirculation of the liquid throughout the system.

14 Claims, 1 Drawing Figure

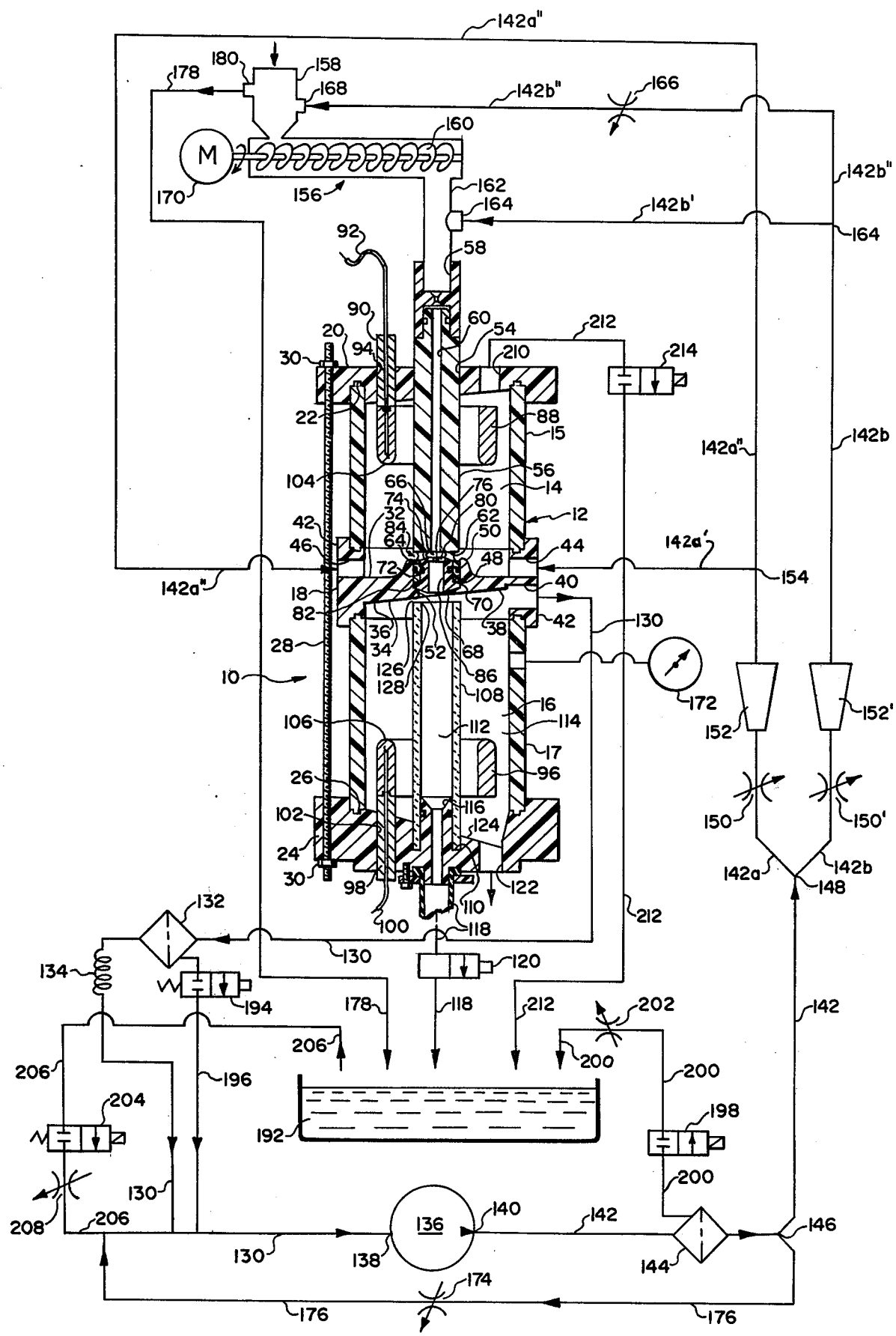

PARTICLE ANALYZING APPARATUS AND FLUID CIRCULATING SYSTEM THEREFOR

BACKGROUND OF THE INVENTION

1. Field of the Invention

This invention relates generally to apparatus for studying the physical properties of particles carried in suspension and more particularly to such apparatus and fluid circulating system therefor for use in connection with analysis of particles having considerable size and density.

2. Description of the Prior Art

There is a need in many fields concerned with particulate substances and aggregates to analyze such particles and determine various characteristics thereof. For example, analysis of such particles, often called "large particles", is required in fields concerned with granulated metals, sands, powders and the like.

One manner of performing analyses on such large particles is with the use of sieve shakers which include meshed screens or sieves into which the particulate material or aggregate is deposited. Analysis of large particles with the use of such sieve shakers gives rise to many disadvantages such as excessive time required to perform the analyses, the need to calibrate individual sieves due to wear and the need to clean the sieves before each re-use thereof.

Attempts have been made to provide electronic particle study apparatus suitable for performing analyses of such large particles while obviating the disadvantages of sieve shakers. One such electronic particle study apparatus is disclosed in U.S. Pat. No. 3,688,191 utilizing structure termed "a Coulter scanning aperture means" as defined in U.S. Pat. No. 2,656,508 (the mark "Coulter" is a Registered Trademark, Registration No. 995,825, of Coulter Electronics, Inc. of Hialeah, Florida). The structure of said U.S. Pat. No. 3,688,191 includes a pair of chambers separated by a Coulter scanning aperture means to perform the large particle analyses desired.

While the structure of U.S. pat. No. 3,686,191 improved upon the sieve shaker method of large particle analyses, other problems occurred in the use of such structure. The patented structure requires that the large particles to be analyzed be maintained in a homogeneous suspension which is difficult to achieve even with the use of an agitation device as disclosed in the patent. Further, the structure of the patented apparatus is such that particles which have been sensed by the Coulter scanning aperture means tend to accumulate and built up behind the aperture resulting in spurious signals being produced. Additionally, often it is desired to change the size of the aperture in such structure so that analyses of different sized particles may be made; the said patented apparatus does not provide convenient means for easily accomplishing removal of one aperture and assembling within the apparatus a different sized aperture.

It also is known that providing for straight line passage of the particles to be analyzed through the center of the aperture by use of a director member will improve the signals detected by a Coulter scanning aperture means. The ratio of the size of the aperture with the distance thereof to the end of the director is known preferably to be maintained constant for optimum results. The provision of such straight line passage of particles through the aperture can be achieved by hydrodynamic focusing thereof together with introduction of sheath flow liquid at the location where the particles are introduced into the aperture. The teaching of such principals can be found in the following patents and publications: U.S. Pat. Nos. 3,831,087, 3,810,010 and 3,793,587; German published patent application No. 2,050,847; P. Crosland-Taylor, et al., "An Electronic Blood-Cell Counting Machine", Blood, Vol. 13, No. 4, April, 1958, pp. 398–409; P. Crosland-Taylor, "A Device for Counting Small Particles suspended in a Fluid through a Tube", Nature, Vol. 171, No. 4340, January, 1953, pp. 37–38. Further, to avoid consuming large volumes of fluids which pass through the relatively large sized apertures used in analyzing large particles, it is known to provide for a closed system in which the fluid continuously is pumped back for recirculation through the system.

Although the various principals referred to have been acknowledged separately in the art as contributing to the achievement of a highly desirable particle analysis apparatus and system, these principals have not heretofore been included together in an advantageously cooperative manner to produce a commercially acceptable apparatus. The present invention employs these principals in a novel structure to provide a highly efficient and compact apparatus and system for analyzing large particles without the disadvantages of the prior art structures.

SUMMARY OF THE INVENTION

The invention provides a particle measuring apparatus and fluid supply system therefor including a housing with a demountable aperture retaining member positioned therein. The aperture retaining member includes an elongate director tube and an aperture holder having an aperture and being removably retained proximate the terminus of the director tube but spaced a small distance therefrom. The downstream side of the aperture is in liquid communication through a conduit system with the upstream side thereof and a pump is interposed in the conduit system to enable continuous recirculation of liquid introduced therein. Particles introduced to the director tube are directed through the center of the aperture; clean ensheathing liquid is provided for entry through the space between the aperture and the terminus of the director tube for passage thereof through the aperture simultaneously with passage of the particles.

BRIEF DESCRIPTION OF THE DRAWING

The FIGURE illustrates a sectional view of the housing and aperture retaining member of the invention together with a fluid circulation system therefor, the said fluid circulation system being shown schematically.

DESCRIPTION OF THE PREFERRED EMBODIMENT

Referring to the drawing, the apparatus 10 of the invention which preferably is generally cylindrical in configuration and is formed of optically-clear material is shown in longitudinal section. The apparatus 10 includes a housing 12 having an upper chamber 14 defined by a cylindrical wall 15 and a lower chamber 16 defined by a cylindrical wall 17 with a centrally-located wall 18 dividing the two chambers. A top cap member 20 having a circumferential groove 22 for receipt of the upper edge of the cylindrical wall 15 closes off the upper chamber 14 and a bottom cap member 24 with a similar circumferential groove 26 for receipt of the lower edge of the cylindrical wall 17 closes off the lower chamber 16. The several parts of the housing 12 are retained assembled together as shown by one or more connecting rods 28 and securing nuts 30.

The centrally-located wall 18 has a top surface 32 forming the bottom of upper chamber 14; the surface 32 is disposed generally normal with respect to the cylindrical walls 15, 17. Centrally-located wall 18 also has a bottom surface 34 forming the top of lower chamber 16; the surface 34 is disposed at an angle with respect to the cylindrical walls 15, 17 so that the cross-sectional dimension of the wall 18 is greater adjacent one side 36 than at the opposite side 38 thereof. A single port 40 opens to a flange 42 of the wall 18 on the bottom side thereof proximate the side 38 of wall 18 to provide an opening from lower chamber 16. Two ports 44, 46 open to the flange 42 on the top side of wall 18 at spaced locations on the flange to provide two openings from upper chamber 14.

The centrally-located wall 18 has a passageway 48 formed therein connecting the chambers 14 and 16. The passageway 48 has an annular lip 50 facing the upper chamber 14 and a ledge 52 formed proximate the bottom surface 34 of the wall 18 such that the cross-sectional dimension of the passageway 48 is reduced at the lower end thereof.

Top cap member 20 also is provided with a passageway 54 which is positioned to be in registry with passageway 48 in wall 18. An elongate cylindrical director 56 is removably positioned through passageway 54 and rests on ledge 52 of passageway 48.

Director 56 has a top funnel part 58 which opens to a precision central bore 60 extending the length of the director. The director has a generally flat terminus 62 defining the end of the bore 60 and a depending flange 64 is formed as an extension of the director. The flange 64 is provided with a plurality of entry slots 66 which open from the terminus 62 of the director to the upper chamber 14.

A cylindrical aperture holder 68 having an annularly extending flange 70 is removably positioned within the flange 64 of the director 56 with an O-ring 72 disposed between the aperture holder and the flange for fluid-tight seal therebetween. The aperture holder 68 carries on the upper surface 74 thereof facing the terminus 62 of the director a precision bored aperture 76 which may be provided in a jeweled insert 80 as is known. The opening of the director bore 60 at terminus 62 and the aperture 76 are positioned in registry and the aperture diameter and that of the director bore are the same. The annular flange 70 of the aperture holder 68 abuts the lower edge 82 of director flange 64 when the aperture holder is positioned upon the director so as to precisely define the space 84 between the director terminus 62 and the aperture 76. Preferably, the space 84 will be the same as the diameter of the aperture 76 so as to enable operation of the apparatus with optimum efficiency.

The jeweled insert 80 carrying the aperture 76 is disposed in a recess of the aperture holder 68. The underside of the insert 80 faces an enlarged bore 86 which forms an exit opening from the aperture 76 to the lower chamber 16.

An annularly-shaped electrode 88 is disposed in upper chamber 14 to encircle director 56 and has an extension part 90 carrying an electrode wire 92 which passes through an opening 94 in top cap member 20. A similar electrode 96 is disposed in lower chamber 16 and has an extension part 98 carrying an electrode wire 100 which passes through an opening 102 in bottom cap member 24. Preferably, the electrodes 88, 96 are formed of metal coated ceramic and have rounded chamber-facing surfaces 104, 106 to prevent accumulation thereon of particles which will be present in the apparatus 10 when the same is in operation. Also preferably, the electrode 88 is the ground electrode and electrode 96 is the electrically hot electrode which are connected through the respective electrode wires 92, 100 to a signal detecting instrument (not shown) in a known manner.

A tubular wall 108 is positioned within a slot 110 of bottom cap member 24 and extends to a location proximate the bottom surface 34 of centrally-located wall 18. The tubular wall 108 divides the bottom chamber 16 into two portions, these being a central chamber 112 and a concentric electrode chamber 114. The central chamber 112 opens at the bottom thereof to a passageway 116 in the bottom cap member 24 which is provided with a conduit 118 normally closed by a pinch valve 120. The concentric electrode chamber 114 opens at the bottom thereof to a drain port 122 which normally is closed but may be opened to drain the contents of the chamber. The chamber-facing wall 124 of bottom cap member 24 is slanted toward the drain port 122 to enhance draining of said chamber.

As stated, tubular wall 108 extends to a location proximately bottom surface 34 of centrally-located wall 18. A space 126 is provided between the upper end 128 of the tubular wall 108 and the bottom surface 34 to permit fluid movement out of both chambers 112 and 114 through port 40 out of chamber 16 when desired as will be described.

The apparatus 10 is intended for operation in a fluid circulating system as shown schematically in the FIGURE. A fluid transmitting conduit 130 passes from port 40 in the lower chamber 16 through a vacuum filter 132 and a lengthened coil of conduit 134 to a constant speed pump 136. The pump 136 has a vacuum side 138 into which the conduit 130 enters and an opposite pressure side 140 with a conduit 142 connected thereto. Conduit 142 passes through a filter 144 and past junction 146 to junction 148 where the conduit 142 is split into two conduits 142*a* and 142*b*. Conduit 142*a* passes through a valve 150 and a flow gauge 152 and thereafter is split at junction 154 into conduit 142*a'* and 142*a"*. Each of conduits 142*a'* and 142*a"* re-enter the apparatus 10 at respective ports 44, 46 which open to upper chamber 14.

The funnel part 58 of director 56 has a feed device 156 associated therewith which is illustrated as being an auger feed device. It is to be understood that any of a wide variety of feed devices may be employed. The feed device 156 includes a hopper 158 leading to an auger 160 which terminates at a feed tube 162 opening to the funnel part 58. Conduit 142*b* leading from junction 148 passes through a valve 150' and a flow gauge 152' and thereafter is split at junction 164 into conduit 142*b'* and 142*b"*. Conduit 142*b'* enters feed tube 162 through a port 164 opening thereto and conduit 142*b"*, via a valve 166, enters hopper 158 through a port 168 opening thereto.

The operation of the apparatus 10 and system therefor is as follows. Assuming the chambers 14 and 16 as well as all conduits and the feed device are filled with particle free or clean electrolyte, a sample solution of large particles is deposited in hopper 158 and motor 170 is activated to cause auger 160 to feed the sample solution to funnel part 58. Pump 136 is started to cause a vacuum to be applied through conduit 130 to lower chamber 16 and fluid under pressure to be applied through conduit 142, 142a' and 142a" to upper chamber 14. Large particles enter the director 56 from the funnel part 58 and pass down the long director bore 60 to the terminus 62 thereof.

Particles passing through the director bore 60 tend to move away from the walls thereof by reason of the extended length thereof. Further, particles which may be bunched together when they enter the director bore tend to separate as they pass down toward the terminus 62. Additionally, a particle which reaches the terminus has moved to the center of the director bore and thereby is positioned for passage directly through the center of the aperture 76. Simultaneously with movement of the particles down the director bore 60, the pump 136 causes clean electrolyte to enter the upper chamber 14 through ports 44, 46. The clean electrolyte in chamber 14 enters the space 84 through slots 66 between terminus 62 and the insert 80 and passes as a sheath flow immediately through the aperture to chamber 112. The sheath flow of electrolyte from chamber 14 through the aperture on the upstream side thereof, while the particles which have moved down the director bore 60 pass through the aperture, has a hydrodynamically focusing effect upon said particles to ensure that they are directed and pass immediately through the aperture. As the particles pass through the aperture they are sensed by the detector which is connected between the electrodes 88, 96.

The flow of particles which pass through the aperture 76 enters the enlarged bore 86 of the aperture holder 68 where it jets or spreads away from the aperture on the downstream side thereof to prevent particles from swirling back into the sensing zone in the area immediately surrounding the aperture. The particulate suspension then enters central chamber 112 where heavy particles may fall to the bottom 116 for evacuation during a cleaning operation of the apparatus 10. Lighter particles and the remainder of the suspension is drawn out of the lower chamber 16 through exit port 40.

The majority of the particulate suspension in lower chamber 16 is confined to central chamber 112 thereof and does not enter concentric electrode chamber 114. Thus, the electrode chamber 114 is maintained substantially particle free and there is minimal fluid flow therein resulting in decreased resistance modulation which may produce unwanted signals to the detector connected to the electrodes. Further, by reason of the rounded upper portions 106 of the electrode 96, any particles which may fall thereon will not accumulate on the electrode.

Particulate suspension which passes out of port 40 moves through conduits 130 and filter 132 which removes the particles so that filtered electrolyte passes out of the filter. The fluid next passes through the lengthened coil of conduit 134 which functions to electrically isolate the two sides of the aperture in the conduit in a manner which is known. Thereafter, the fluid passes into and through pump 136 and next through filter 144 which removes any air from the fluid which has accumulated in the conduit or pump. The valve 150 serves to control the flow of sheath fluid into the upper chamber 14 and the gauge 152 enables measurement of the flow thereto. The vacuum draw in lower chamber 16 may be measured by gauge 172 which is connected through a suitable conduit to a port in the chamber wall.

During operation of the apparatus and system it may be desirable to supply added electrolyte to the director 56 and/or to the hopper 158 so as to enhance washing action and movement of the particles through the system. For this purpose, valve 150' may be opened to permit cleaned electrolyte to pass through measuring gauge 152' and re-enter funnel 58 through conduit 142b' and also hopper 158 through conduit 142b". The valves 150, 150' in the conduits leading from junction 148 are operable as a proportioning control to divide the flow of electrolyte between the sheath flow entry at ports 44, 46 and that to the director at port 164 and the hopper at port 168. An overflow conduit 178 passes from an overflow port 180 in hopper 158 to a recovery tank 192 so that electrolyte may be recovered for re-use.

Since pump 136 is a constant speed pump, variation of the pressure produced thereby as desired may be accomplished by adjustment of valve 174 which is disposed in conduit 176 passing on either side of the pump. Opening of the valve 174 will permit fluid to pass around the loop of conduit including conduit 176 and lower the pressure in the conduits 130, 142.

After operation of the apparatus 10 as described it may be desired to clean the filter 132 and recover the large particles trapped therein. To effect such recovery, valve 194 is opened and pump 136 draws particle laden liquid therefrom through conduit 196 and into the pump. During such cleaning operation, valve 198 in conduit 200 leading from filter 144 also is opened so that, by adjustment of valve 202, the pressure flow of fluid will move to recovery tank 192. This operation of recovering particles from filter 132 also serves to purge the same of air which may have accumulated therein. During another operation, the pinch valve 120 in conduit 118 leading from lower chamber 16 also may be opened to recover heavy particles which have accumulated in the central chamber 112. These heavy particles pass through the conduit 118 also into the recovery tank 192.

Upon cleaning of the central chamber 112, the amount of electrolyte liquid in the system will be diminished and it will be desired to replace this liquid from the recovery tank. To do so, valve 204 is opened and pump 136 will draw electrolyte from the tank 192 through the conduit 206 which passes through flow rate adjustment valve 208.

It also may be desired to purge upper chamber 14 of air bubbles which may accumulate at the top thereof. For this purpose, a port 210 in top cap member 20 opens to conduit 212 which, by opening of valve 214, will permit said air bubbles entrained in liquid to pass to recovery tank 192.

It will be appreciated that the construction of apparatus 10 is such that even large and heavy particles may be analyzed without the need for maintaining a uniform suspension thereof as in prior art structures. There is no need to continuously stir the suspension introduced into the hopper 158 so as to maintain such a homogeneous suspension because all such particles pass from the feeder and through the director tube to the particle sensing aperture 76. The apparatus is extremely flexible by reason of the fact that the director 56 easily may be removed from the housing 12 by simply lifting the same from the passageway 54 in the housing and substituting the same with another having a different size aperture and director bore. Thus, the user of the apparatus may have several directors 56 of variant sized bores available for positioning in the housing so as to provide a measurement range of the apparatus within wide limits merely by interchanging such directors. The removability of the aperture holder 68 enables convenient cleaning of the aperture if this becomes necessary; if desired, a substitute holder with a fresh aperture may be assembled on a director and the critical spacing between director terminus and the aperture will be maintained.

To avoid consuming large volumes of electrolyte, the system of the invention continually pumps the electrolyte which passes through the aperture back to the supply side of the apparatus after the same has passed through filters which remove any entrained solids or air.

Minor variations in the structure and other variations in the arrangement and size of the various parts may occur to those skilled in the art without departing from the spirit or circumventing the scope of the invention as set forth in the appended claims.

What is desired to be secured by Letters Patent of United States is:

1. A particle analyzing apparatus and fluid circulating system therefor comprising, a vessel having a first chamber and a second chamber with a wall therebetween separating said chambers, said first chamber including a cap and a passageway in said cap providing access to said first chamber, said wall having a passageway therein providing communication between said first and second chambers, said passageways in the cap and wall being axially aligned one with the other, an elongate director removably positioned within said passageways, said director having a bore therein extending the length thereof from an entrance end to a terminus of the director, an aperture retaining member removably positioned on the director at said terminus, said aperture retaining member having an aperture therein spaced from the director terminus to permit passage of particle free liquid from said first chamber through said aperture and into said second chamber, the aperture and director bore being coaxial, a liquid transmission conduit extending from an opening in said second chamber to at least one opening in said first chamber, means in said liquid transmission conduit for continuously re-circulating particle free liquid from said second chamber back to said first chamber through the space between the director terminus and the aperture to pass through the aperture and return to the second chamber, means to feed particles into said director at the entrance end such that said particles move through the bore to the director terminus, a first electrode in the first chamber and a second electrode in the second chamber to establish an electrical field in the aperture between said chambers, means including electrical leads connected to the electrodes and adapted to extend connections to a detector to respond to electrical measuring signals produced across said electrodes with passage of particles through said aperture, whereby particles introduced to said director will move therethrough and pass through the center of the aperture into the second chamber simultaneously with passage of re-circulated particle free liquid through the aperture.

2. The invention as claimed in claim 1 in which the diameter of the bore in the director is the same as the diameter of the aperture.

3. The invention as claimed in claim 1 in which the director has a depending flange formed as an extension of the terminus, said flange having a plurality of slots to permit entry of liquid between the first chamber and the terminus.

4. The invention as claimed in claim 3 in which the aperture retaining member has a circumferentially extending flange and is positioned within the flange of the director with the circumferential flange abutting a lower edge of the director flange so as to precisely define the space between the terminus and the aperture.

5. The invention as claimed in claim 4 in which the space between the terminus and the aperture is equal to the diameter of the aperture.

6. The invention as claimed in claim 3 in which the liquid transmission conduit enters the first chamber at two locations spaced about the perimeter of the vessel.

7. The invention as claimed in claim 1 in which said means to re-circulate particle free liquid comprise a constant speed pump.

8. The invention as claimed in claim 1 in which said apparatus is formed of optically clear material.

9. The invention as claimed in claim 1 in which said second chamber includes a wall dividing the same into a central chamber and an electrode chamber, the flow of liquid through the aperture being substantially into said central chamber, said second electrode being disposed in said electrode chamber.

10. The invention as claimed in claim 9 in which the wall dividing the second chamber extends to a location proximate the wall dividing the first and second chambers but spaced therefrom to permit liquid movement out of the central chamber.

11. The invention as claimed in claim 1 including at least one filter member in the liquid transmission conduit to remove particles from the liquid before the same is re-circulated to the first chamber.

12. The invention as claimed in claim 1 in which said liquid transmission conduit extends also from the second chamber to the entrance of the director.

13. The invention as claimed in claim 12 including liquid flow proportioning control means in the conduit for selectively dividing the liquid flow from the second chamber to the first chamber and the director.

14. The invention as claimed in claim 1 in which the means to feed particles into the director comprise an auger.

* * * * *